(12) United States Patent
Zhao et al.

(10) Patent No.: US 11,065,460 B2
(45) Date of Patent: Jul. 20, 2021

(54) BATTERY ASSEMBLY FOR MEDICAL DEVICE

(71) Applicant: Medtronic, Inc., Minneapolis, MN (US)

(72) Inventors: Hailiang Zhao, Plymouth, MN (US); Steven J. May, Minnetonka, MN (US)

(73) Assignee: Medtronic, Inc., Minneapolis, MN (US)

(*) Notice: Subject to any disclaimer, the term of this patent is extended or adjusted under 35 U.S.C. 154(b) by 67 days.

(21) Appl. No.: 16/426,849

(22) Filed: May 30, 2019

(65) Prior Publication Data

US 2020/0381693 A1  Dec. 3, 2020

(51) Int. Cl.
*A61N 1/378* (2006.01)
*H01M 50/529* (2021.01)
*H01M 50/531* (2021.01)

(52) U.S. Cl.
CPC .......... *A61N 1/378* (2013.01); *H01M 50/529* (2021.01); *H01M 50/531* (2021.01); *H01M 2220/30* (2013.01)

(58) Field of Classification Search
CPC ...... H01M 2/24; H01M 2/26; H01M 2220/30; H01M 50/529; H01M 50/531; A61N 1/378
See application file for complete search history.

(56) References Cited

U.S. PATENT DOCUMENTS

| 5,419,982 | A | 5/1995 | Tura et al. |
| 6,032,075 | A | 2/2000 | Pignato et al. |
| 7,035,078 | B1 | 4/2006 | Viavattine |
| 7,111,882 | B2 | 9/2006 | Corscadden et al. |
| 7,179,562 | B2 | 2/2007 | Zolotnik et al. |
| 7,479,349 | B2 | 1/2009 | O'phelan et al. |
| 7,564,677 | B2 | 7/2009 | Poplett |
| 8,133,604 | B1 | 3/2012 | Nakahara et al. |
| 8,236,411 | B2 | 8/2012 | Waki et al. |
| 8,236,441 | B2 | 8/2012 | Gardner et al. |
| 8,614,017 | B2 | 12/2013 | Viavattine |

(Continued)

FOREIGN PATENT DOCUMENTS

| EP | 1798787 A2 | 6/2007 |
| EP | 3405257 A1 | 11/2018 |
| WO | 2017127149 A1 | 7/2017 |

OTHER PUBLICATIONS

U.S. Appl. No. 62/835,738, filed Apr. 18, 2019, naming inventors Louwagie et al.

(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

In some examples, a battery assembly for an implantable medical device may include an electrode stack comprising a plurality of electrode plates. The plurality of electrode plates may comprise a first electrode plate including a first tab extending from the first electrode plate and a second electrode plate including a second tab extending from the second electrode plate, an alignment member extending through the first tab and the second tab, and a weld on a side of the electrode stack extending from the first tab to the second tab, wherein the weld penetrates into the alignment member.

20 Claims, 8 Drawing Sheets

(56) References Cited

U.S. PATENT DOCUMENTS

| | | |
|---|---|---|
| 8,841,020 B2 | 9/2014 | Viavattine |
| 2003/0171784 A1 | 9/2003 | Dodd et al. |
| 2003/0199942 A1 | 10/2003 | Nielsen et al. |
| 2006/0096082 A1 | 5/2006 | Aamodt et al. |
| 2006/0166088 A1 | 7/2006 | Hokanson et al. |
| 2006/0222942 A1 | 10/2006 | Zhao et al. |
| 2009/0197160 A1 | 8/2009 | Fujiwara et al. |
| 2009/0197180 A1* | 8/2009 | Viavattine ............ H01M 2/1646 429/246 |
| 2009/0208816 A1 | 8/2009 | Viavattine et al. |
| 2012/0107670 A1* | 5/2012 | Viavattine ......... H01M 10/0436 429/153 |
| 2013/0131744 A1* | 5/2013 | Viavattine ............... H01M 6/46 607/5 |
| 2013/0131745 A1 | 5/2013 | Viavattine |
| 2020/0330774 A1* | 10/2020 | Louwagie ............ A61N 1/3758 |

OTHER PUBLICATIONS

U.S. Appl. No. 16/841,157, filed Apr. 6, 2020, by Louwagie et al.
U.S. Appl. No. 15/530,470, filed Aug. 2, 2019, by Zhao.

* cited by examiner

BATTERY ASSEMBLY FOR MEDICAL DEVICE

TECHNICAL FIELD

The disclosure relates to batteries and, more particularly, to batteries of medical devices.

BACKGROUND

Medical devices such as implantable medical devices (IMDs) include a variety of devices that deliver therapy (such as electrical simulation or drugs) to a patient, monitor a physiological parameter of a patient, or both. IMDs typically include a number of functional components encased in a housing. The housing is implanted in a body of the patient. For example, the housing may be implanted in a pocket created in a torso of a patient. The housing may include various internal components such as batteries and capacitors to deliver energy for therapy delivered to a patient and/or to power circuitry for monitoring a physiological parameter of a patient and controlling the functionality of the medical device.

SUMMARY

In some aspects, the disclosure is directed to battery assemblies for use, e.g., in a medical device, and techniques for manufacturing the battery assemblies.

In one example, the disclosure is directed to a battery assembly for an implantable medical device, the assembly comprising an electrode stack comprising a plurality of electrode plates, wherein the plurality of electrode plates comprises a first electrode plate including a first tab extending from the first electrode plate and a second electrode plate including a second tab extending from the second electrode plate; an alignment member extending through the first tab and the second tab; and a weld on a side of the electrode stack extending from the first tab to the second tab, wherein the weld penetrates into the alignment member.

In another example, the disclosure is directed to a method for forming a battery assembly, the method comprising assembling an electrode stack on an alignment member, the electrode stack comprising a plurality of electrode plates, wherein the plurality of electrode plates comprises a first electrode plate including a first tab extending from the first electrode plate and a second electrode plate including a second tab extending from the second electrode plate, wherein the alignment member extends through the first tab and the second tab when the electrode stack is assembled; and welding a side of the electrode stack to form a weld that penetrates into the alignment member through the first tab and the second tab.

The details of one or more examples of the disclosure are set forth in the accompanying drawings and the description below. Other features, objects, and advantages of the disclosure will be apparent from the description and drawings, and from the claims.

DETAILED DESCRIPTION

Figure 1:
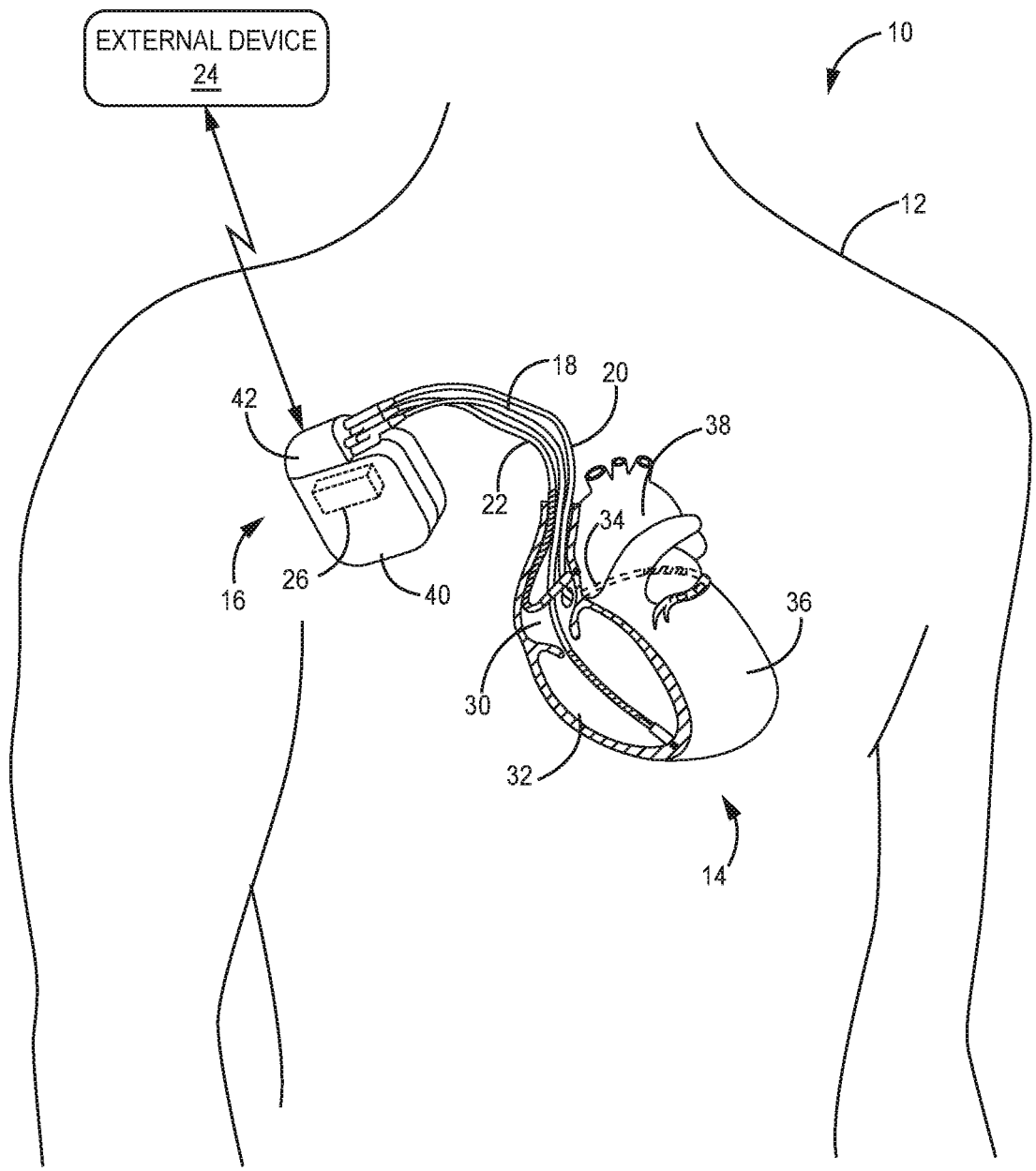
FIG. 1 is a conceptual diagram that illustrates an example medical device system that may be used to deliver therapy to a patient.

A variety of medical devices may utilize one or more batteries as a power source for operational power. For example, an implantable medical device (IMD) that provides cardiac rhythm management therapy to a patient may include a battery to supply power for the generation of electrical therapy or other functions of the IMD. For ease of illustration, examples of the present disclosure will be described primarily with regard to batteries employed in IMDs that provide cardiac rhythm management therapy. However, as will be apparent from the description herein, examples of the disclosure are not limited to IMDs that provide such therapy. For example, in some instances, one or more of the example batteries describe herein may be used by a medical device configured to deliver electrical stimulation to a patient in the form of neurostimulation therapy (e.g., spinal cord stimulation therapy, deep brain stimulation therapy, peripheral nerve stimulation therapy, peripheral nerve field stimulation therapy, pelvic floor stimulation therapy, and the like). In some examples, example batteries of this disclosure may be employed in medical device configured to monitor one or more patient physiological parameters, e.g., by monitoring electrical signals of the patient, alone or in conjunction with the delivery of therapy to the patient.

In some examples, a battery of an IMD may include a plurality of electrode plates (e.g., including both anode and cathode plates) stacked on each other in which each of the plates includes a tab extending therefrom. The tabs of the anode plates may be aligned with each other in a stack and electrically connected to each other to form an anode of the battery. In this sense, the tab stack may function as an electrical interconnect between the plates of the anode. Similarly, the tabs of the cathode plates may be aligned with each other in a stack and electrically connected to each other to form a cathode of the battery. In some examples, such a battery may be refereed to as a flat plate battery.

In some examples, in each of the anode tab stack and cathode tab stack, a spacer may be located between adjacent individual tabs in the stack of tabs, e.g., such that each individual tab is separated from an adjacent tab by a spacer. The spacers may be electrically conductive to electrically couple the respective tabs in the stack to each other and define an interconnect between respective plates of the electrode. For each electrode, the tabs in the stack of tabs and spacers may be attached to each other by one or more side laser welds that span the height of the tab stack.

During assembly, the electrode plates may be stacked using a fixture pin for alignment. Each tab of the plates may include an aperture, e.g., in the center of the tab, that is inserted onto the fixture pin. The tabs of the plates may be sequentially inserted onto the fixture pin along with any spacers between the tabs to stack the plates with the tabs aligned with each other and spaced as desired. Once stacked, the side of the tab stack may be welded to attach the tabs and spacers to each other as a stack of electrode plates. The stack of electrode plates may then be removed from the fixture pin and then sealed within a battery housing.

During the welding process, the location of the side weld and penetration depth of the weld into the tabs must be carefully controlled to avoid penetrating the weld into the apertures formed in the tabs and any spacers. In such an example, penetration into the apertures may cause melting around the apertures and damage the fixture pin that is present during the welding process.

In some examples, the stack of electrode plates may be subject to "fanning" (e.g., opening like the pages of a bound book) or other forces, e.g., as a result of the mechanical force applied by the expansion of the electrode stack during discharge of the battery. In some examples, the applied force may result in a concentration of stress at the root of the side weld(s) attaching the plates and spacers to each other. Such stress may cause the weld(s) to fail resulting in undesirable electrical connection between the electrodes and leading to reduced battery capacity and power capability. Weld failure may also result in a spacer breaking away from the stack and may cause internal shorting and undesired reduction of battery capacity and power.

In accordance with at least some examples of the disclosure, a battery assembly that includes an electrode tab stack may include an alignment member, e.g., a conductive pin, that extends through a stack of tabs, e.g., via apertures formed in the respective tabs. The battery assembly may include a side weld that penetrates through the tabs into the alignment member. In examples in which the stack of tabs includes spacers between the respective tabs in the stack, the side weld may also penetrate through the spacers into the alignment member. The battery assembly may also include one or more side welds penetrating into the tab stack on one or both side of the alignment member.

In some examples, the alignment pin may be used during the assembly of the electrode plates. For example, the respective tabs of electrode plates may be sequentially stack onto the alignment pin by way of apertures formed in each respective tab. Thus, alignment pin may serve as a fixture pin during assembly where the alignment pin is then welded as part of the stack rather than being removed after assembly. In this aspect, the alignment pin may be referred to as a consumable pin that is incorporated into the final battery assembly rather than a fixture pin that is used only during the assembly of the battery assembly. Since the alignment member is consumable rather than a fixture pin, any side welds that are located on either side of the pin, e.g., in addition to a side weld that penetrates into the alignment pin, may be formed without concern of penetrating too close to the alignment member, e.g., to allow for deeper weld penetration into the side of the stack.

In some examples, the alignment member may be an electrically conductive member, such as an electrically conductive alignment pin. For example, the electrically conductive alignment pin may be a titanium pin or pin formed of another conductive material. The electrically conductive member may provide for electrical interconnection between the respective tabs of the electrode plates.

Examples of the disclosure may provide for one or more benefits. In some examples, the use of an electrically conductive consumable pin or other alignment member that is welded to the tab stack may be resistant to stresses that may otherwise be present during consumption of the battery, e.g., because the stress concentration at the root of the weld may be substantially eliminated or otherwise reduced. The additional side weld into the alignment pin may be much stronger, e.g., because of the elimination or reduction in stress concentration in use condition. For example, during the consumption of the battery, the thickness of the stack of electrodes may increase, causing the welded stacks of spacers and tabs to open like a fan. Under such a loading condition, the gaps between the spacers and tabs may form sharp notches at the root of the weld. The sharp notches may serve to increase stress concentration at the root of the weld, making the weld to crack easily. When a pin is welded into the stack, the notches are removed from the root of the weld and therefore, stress concentration may be eliminated at the root of the weld, enabling the weld to withstand much higher load.

While examples of the present disclosure are described with regard to a battery assembly including an alignment member as part of the tab stack, where the assembly includes a side weld that penetrates into the side of the stack into the alignment member, the use of the term "alignment" does not necessarily require that that alignment member be used to align the respective tabs during assembly of the battery stack. In some examples, the alignment member may be placed within apertures of the respective tabs after the tabs have been suitably aligned with each other, at which time a side weld may be performed to weld the alignment member to the tab stack. In other examples, the alignment member may be used during assembly of the electrode plates by stacking the tabs onto each other using the alignment member as a fixture pin that is then welded to the stack of tabs, as described herein.

FIG. 1 is a conceptual diagram that illustrates an example medical device system 10 that may be used to provide electrical therapy to a patient 12. Patient 12 ordinarily, but not necessarily, will be a human. System 10 may include an IMD 16, and an external device 24. In the example illustrated in FIG. 1, IMD 16 has battery 26 positioned within an outer housing 40 of the IMD 16. Battery 26 may be a primary or secondary battery.

While the examples in the disclosure are primarily described with regard to battery 26 positioned within housing 40 of IMD 16 for delivery of electrical therapy to heart of patient 12, in other examples, battery 26 may be utilized with other implantable medical devices. For example, battery 26 may be utilized with an implantable drug delivery device, an implantable monitoring device that monitors one or more physiological parameter of patient 12, an implantable neurostimulator (e.g., a spinal cord stimulator, a deep brain stimulator, a pelvic floor stimulator, a peripheral nerve stimulator, or the like), or the like. Moreover, while examples of the disclosure are primarily described with regard to implantable medical devices, examples are not limited as such. Rather, some examples of the batteries described herein may be employed in any medical device including non-implantable medical devices. For example, an example battery may be employed to supply power to a medical device configured delivery therapy to a patient externally or via a transcutaneously implanted lead or drug delivery catheter.

In the example depicted in FIG. 1, IMD 16 is connected (or "coupled") to leads 18, 20, and 22. IMD 16 may be, for example, a device that provides cardiac rhythm management therapy to heart 14, and may include, for example, an implantable pacemaker, cardioverter, and/or defibrillator that provides therapy to heart 14 of patient 12 via electrodes coupled to one or more of leads 18, 20, and 22. In some examples, IMD 16 may deliver pacing pulses, but not cardioversion or defibrillation shocks, while in other examples, IMD 16 may deliver cardioversion or defibrillation shocks, but not pacing pulses. In addition, in further examples, IMD 16 may deliver pacing pulses, cardioversion shocks, and defibrillation shocks.

IMD 16 may include electronics and other internal components necessary or desirable for executing the functions associated with the device. In one example, IMD 16 includes one or more of processing circuitry, memory, a signal generation circuitry, sensing circuitry, telemetry circuitry, and a power source. In general, memory of IMD 16 may include computer-readable instructions that, when executed by a processor of the IMD, cause it to perform various functions attributed to the device herein. For example, processing circuitry of IMD 16 may control the signal generator and sensing circuitry according to instructions and/or data stored on memory to deliver therapy to patient 12 and perform other functions related to treating condition(s) of the patient with IMD 16.

IMD 16 may include or may be one or more processors or processing circuitry, such as one or more digital signal processors (DSPs), general purpose microprocessors, application specific integrated circuits (ASICs), field programmable logic arrays (FPGAs), or other equivalent integrated or discrete logic circuitry. Accordingly, the term "processor" and "processing circuitry" as used herein may refer to any of the foregoing structure or any other structure suitable for implementation of the techniques described herein.

Memory may include any volatile or non-volatile media, such as a random-access memory (RAM), read only memory (ROM), non-volatile RAM (NVRAM), electrically erasable programmable ROM (EEPROM), flash memory, and the like. Memory may be a storage device or other non-transitory medium.

The signal generation circuitry of IMD 16 may generate electrical therapy signals that are delivered to patient 12 via electrode(s) on one or more of leads 18, 20, and 22, in order to provide pacing signals or cardioversion/defibrillation shocks, as examples. The sensing circuitry of IMD 16 may monitor electrical signals from electrode(s) on leads 18, 20, and 22 of IMD 16 in order to monitor electrical activity of heart 14. In one example, the sensing circuitry may include switching circuitry to select which of the available electrodes on leads 18, 20, and 22 of IMD 16 are used to sense the heart activity. Additionally, the sensing circuitry of IMD 16 may include multiple detection channels, each of which includes an amplifier, as well as an analog-to-digital converter for digitizing the signal received from a sensing channel (e.g., electrogram signal processing by processing circuitry of the IMD).

Telemetry circuitry of IMD 16 may be used to communicate with another device, such as external device 24. Under the control of the processing circuitry of IMD 16, the telemetry circuitry may receive downlink telemetry from and send uplink telemetry to external device 24 with the aid of an antenna, which may be internal and/or external.

The various components of IMD 16 may be coupled to a power source such as battery 26, which may be a lithium primary battery. Battery 26 may be capable of holding a charge for several years. In general, battery 26 may supply power to one or more electrical components of IMD 16, such as, e.g., the signal generation circuitry, to allow IMD 16 to deliver therapy to patient 12, e.g., in the form of monitoring one or more patient parameters, delivery of electrical stimulation, or delivery on a therapeutic drug fluid. Battery 26 may include a lithium-containing anode and cathode including an active material that electrochemically reacts with the lithium within an electrolyte to generate power.

Leads 18, 20, 22 that are coupled to IMD 16 may extend into the heart 14 of patient 12 to sense electrical activity of heart 14 and/or deliver electrical therapy to heart 14. In the example shown in FIG. 1, right ventricular (RV) lead 18 extends through one or more veins (not shown), the superior vena cava (not shown), and right atrium 30, and into right ventricle 32. Left ventricular (LV) coronary sinus lead 20 extends through one or more veins, the vena cava, right atrium 30, and into the coronary sinus 34 to a region adjacent to the free wall of left ventricle 36 of heart 14. Right atrial (RA) lead 22 extends through one or more veins and the vena cava, and into the right atrium 30 of heart 14. In other examples, IMD 16 may deliver therapy to heart 14 from an extravascular tissue site in addition to or instead of delivering therapy via electrodes of intravascular leads 18, 20, 22. In the illustrated example, there are no electrodes located in left atrium 36. However, other examples may include electrodes in left atrium 36.

IMD 16 may sense electrical signals attendant to the depolarization and repolarization of heart 14 (e.g., cardiac signals) via electrodes (not shown in FIG. 1) coupled to at least one of the leads 18, 20, and 22. In some examples, IMD 16 provides pacing pulses to heart 14 based on the cardiac signals sensed within heart 14. The configurations of electrodes used by IMD 16 for sensing and pacing may be unipolar or bipolar. IMD 16 may also deliver defibrillation therapy and/or cardioversion therapy via electrodes located on at least one of the leads 18, 20, and 22. IMD 16 may detect arrhythmia of heart 14, such as fibrillation of ventricles 32 and 36, and deliver defibrillation therapy to heart 14 in the form of electrical shocks. In some examples, IMD 16 may be programmed to deliver a progression of therapies (e.g., shocks with increasing energy levels), until a fibrillation of heart 14 is stopped. IMD 16 may detect fibrillation by employing one or more fibrillation detection techniques known in the art. For example, IMD 16 may identify cardiac parameters of the cardiac signal (e.g., R-waves, and detect fibrillation based on the identified cardiac parameters).

In some examples, external device 24 may be a handheld computing device or a computer workstation. External device 24 may include a user interface that receives input from a user. The user interface may include, for example, a keypad and a display, which may be, for example, a cathode ray tube (CRT) display, a liquid crystal display (LCD) or light emitting diode (LED) display. The keypad may take the form of an alphanumeric keypad or a reduced set of keys associated with particular functions. External device 24 can additionally or alternatively include a peripheral pointing device, such as a mouse, via which a user may interact with the user interface. In some embodiments, a display of external device 24 may include a touch screen display, and a user may interact with external device 24 via the display.

A user, such as a physician, technician, other clinician or caregiver, or the patient, may interact with external device 24 to communicate with IMD 16. For example, the user may interact with external device 24 to retrieve physiological or diagnostic information from IMD 16. A user may also interact with external device 24 to program IMD 16 (e.g., select values for operational parameters of IMD 16).

External device 24 may communicate with IMD 16 via wireless communication using any techniques known in the art. Examples of communication techniques may include, for example, low frequency or radiofrequency (RF) telemetry, but other techniques are also contemplated. In some examples, external device 24 may include a communication head that may be placed proximate to the patient's body near the IMD 16 implant site in order to improve the quality or security of communication between IMD 16 and external device 24.

In the example depicted in FIG. 1, IMD 16 is connected (or "coupled") to leads 18, 20, and 22. In the example, leads 18, 20, and 22 are connected to IMD 16 using the connector block 42. For example, leads 18, 20, and 22 are connected to IMD 16 using the lead connector ports in connector block 42. Once connected, leads 18, 20, and 22 are in electrical contact with the internal circuitry of IMD 16. Battery 26 may be positioned within the housing 40 of IMD 16. Housing 40 may be hermetically sealed and biologically inert. In some examples, housing 40 may be formed from a conductive material. For example, housing 40 may be formed from a material including, but not limited to, titanium, stainless steel, among others.

Figure 2:
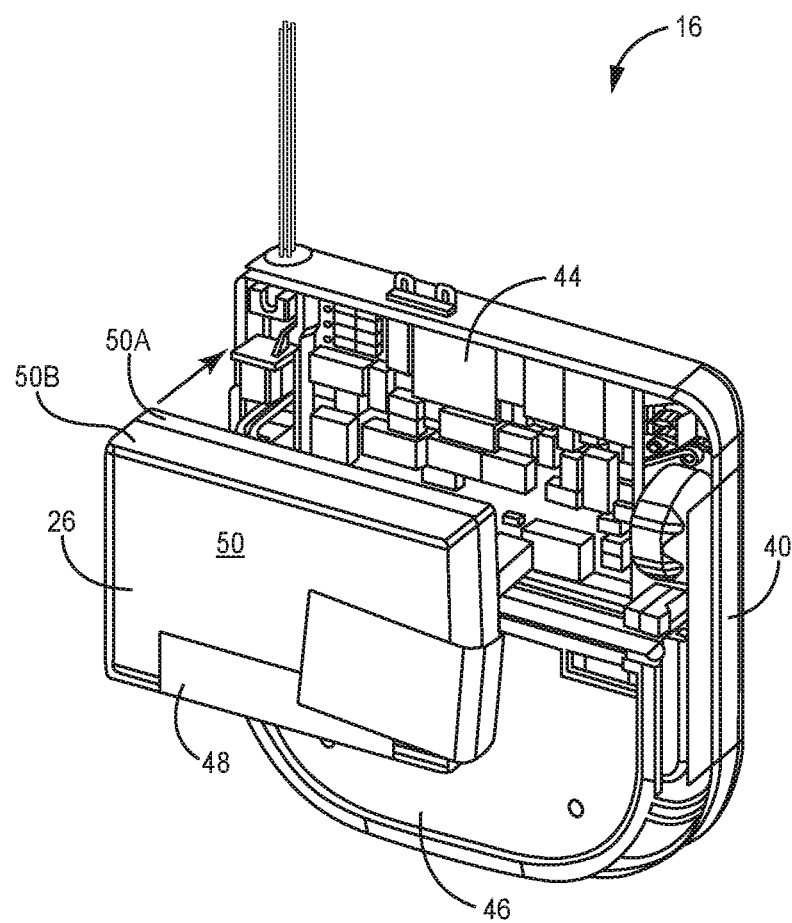
FIG. 2 is a conceptual diagram illustrating a partial exploded view of the IMD of FIG. 1.

FIG. 2 is a conceptual diagram of IMD 16 of FIG. 1 with connector block 42 not shown and a portion of housing 40 removed to illustrate some of the internal components within housing 40. IMD 10 includes housing 40, a control circuitry 44 (which may include processing circuitry), battery 26 (e.g., an organic electrolyte battery) and capacitor(s) 46. Control circuitry 44 may be configured to control one or more sensing and/or therapy delivery processes from IMD 16 via leads 18, 20, and 22 (not shown in FIG. 2). Battery 26 includes battery assembly housing 50 and insulator 48 (or liner) disposed therearound. Battery 26 charges capacitor(s) 46 and powers control circuitry 44.

Figure 3:
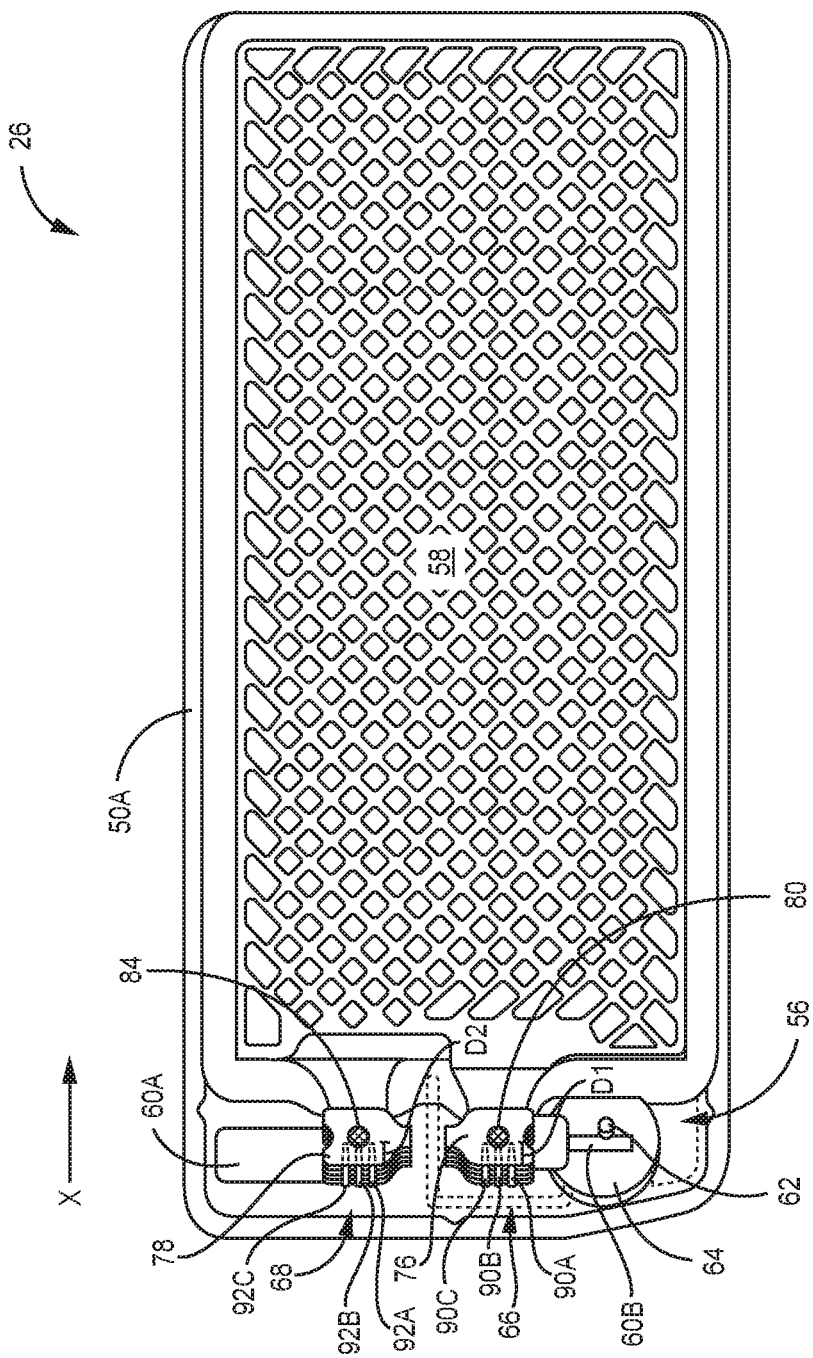
FIGS. 3 and 4 are conceptual diagrams illustrating portions of an example battery assembly in accordance with examples of the disclosure.
Figure 4:
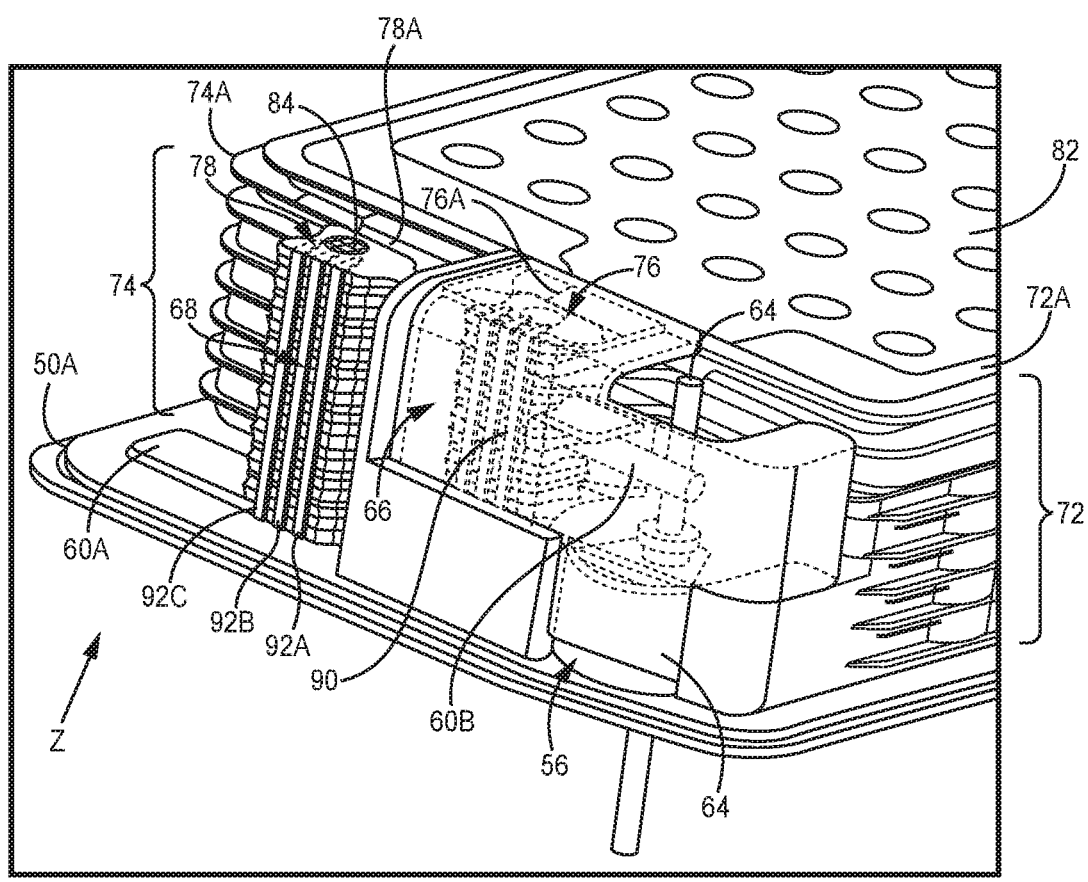

FIGS. 3 and 4 are conceptual diagrams illustrating aspect of example battery 26. Battery 26 includes assembly housing 50 having a bottom housing portion 50A and top housing portion 50B (shown in FIG. 2), a feed-through terminal 56, and an electrode assembly 58. An electrolyte may be filled into the enclosure via a fill port (not shown) in housing 50. Housing 50 houses electrode assembly 58 with the electrolyte. Top portion 50B and bottom portion 50A of housing may be welded or otherwise attached to seal the enclosed components of battery 26 within housing 50. Feed-through assembly 56, formed by pin 62 and insulator member/ferrule 64, is electrically connected to jumper pin 60B. The connection between pin 62 and jumper pin 60B allows delivery of positive charge from electrode assembly 58 to electronic components outside of battery 26.

As noted above, a fill port (not shown) allows for the introduction of liquid electrolyte to electrode assembly 58. The electrolyte creates an ionic path between anode 66 and cathode 68 of electrode assembly 58. The electrolyte serves as a medium for migration of ions between anode 66 and cathode 68 during an electrochemical reaction with these electrodes.

Electrode assembly 58 is depicted as a stacked assembly. Cathode 66 comprises a set of electrode plates 72 (cathode electrode plates) with a set of tabs 76 extending therefrom in a stacked configuration. Alignment member 80 extends through tabs 76 vertically, e.g., in approximately the z-direction labelled in FIG. 4, from the top tab to the bottom tab of set of tabs 76. Side welds 90A-90C (collectively referred to as side welds 90) are located on the side of the set of tabs 76 and penetrate into tabs 76 in approximately the Z-direction (as labelled in FIG. 3). Side welds 90 may attach the respective individual tabs of set of tabs 76 to each other (e.g., in additions to spacers that may be located between respective tabs in the stack).

In accordance with some examples the disclosure, side weld 90B penetrates through tabs 76 into alignment member 80 such that a weld includes a portion of alignment member 80. Conversely, welds 90A and 90C on either side of alignment member 80 penetrate into tabs 76 but not into alignment member 80. In other examples, only a single side weld 90B formed into alignment pin 80 may be present without welds 90A or 90C on either side. Alternatively, or additionally, multiple side welds may penetrate into alignment member 80 and/or one or multiple welds not penetrating into alignment member 80 may be on one or both sides of side weld 90B. As will be described further below, in some examples, alignment member 80 may serve as an alignment and/or registration fixture when the plates 72 are stacked, e.g., by placing respective tabs 76 of plates onto alignment member 80 using apertures formed in tabs 76.

As shown in FIG. 3, welds 90 penetrate into the side of tabs 76 in the X-direction to a depth of D1. Based on the shape and size of tabs 76 and alignment member 80, at a depth of D1, weld 90B penetrates into alignment member 80 such that the weld includes a portion of alignment member 80. In some examples, welds 90A-90C each penetrate to the same depth while in other examples, 90A-90C may have varying depths of penetration. In some examples, D1 may be at least about 0.025 inches. Other depths are contemplated. Welds 90 may not penetrate through tabs 76 into plates 72.

Each electrode plate 72A includes a current collector or grid 82, a tab 76A extending therefrom, and an electrode material. Tabs 76 (e.g., tab 76A) comprises a conductive material (e.g., aluminum, titanium, copper, and/or the like). Electrode material (or cathode material) may include metal oxides (e.g., vanadium oxide, silver vanadium oxide (SVO), manganese dioxide, etc.), carbon monofluoride and hybrids thereof (e.g., CFx+MnO2), combination silver vanadium oxide (CSVO), lithium ion, other rechargeable chemistries, or other suitable compounds.

Anode 68 may be constructed in a similar manner as anode 66. Anode 68 includes a set of electrode plates 74 (anode electrode plates) with a set of tabs 78 extending therefrom in a stacked configuration. Alignment member 84 extends through tabs 78 vertically, e.g., in approximately the z-direction labelled in FIG. 4, from the top tab to the bottom tab of set of tabs 78. Alignment member 84 and set of tabs may be electrically coupled to conductive member 60A, which may be shaped as a plate, and may comprise titanium, niobium, tantalum, vanadium or other suitable materials. Conductive member 60A allows anode 68 to be electrically coupled to electronic components outside of battery 26.

Side weld 92A-92C (collectively referred to as side welds 92) are located on the side of the set of tabs 78 and penetrate into tabs 78 in approximately the Z-direction (as labelled in FIG. 3). Side welds 92 may attach the respective individual tabs of set of tabs 78 to each other (e.g., in additions to spacers that may be located between respective tabs in the stack).

In accordance with some examples the disclosure, side weld 92B penetrates through tabs 78 into alignment member 84 such that a weld includes a portion of alignment member 84. Conversely, welds 92A and 92C on either side of alignment member 84 penetrate into tabs 78 but not into alignment member 84. In other examples, only a single side weld 92B formed into alignment pin 84 may be present without welds 92A or 92C on either side. Alternatively, or additionally, multiple side welds may penetrate into alignment member 84 and/or one or multiple welds not penetrating into alignment member 84 may be on one or both sides of side weld 92B. As will be described further below, in some examples, alignment member 84 may serve as an alignment and/or registration fixture when the plates 74 are stacked, e.g., by placing respective tabs 78 of plates onto alignment member 84 using apertures formed in tabs 78.

As shown in FIG. 3, welds 92 penetrate into the side of tabs 78 in the X-direction to a depth of D2. Based on the shape and size of tabs 78 and alignment member 84, at a depth of D2, weld 92B penetrates into alignment member 84 such that the weld includes a portion of alignment member 84. In some examples, welds 92A-92C each penetrate to the same depth while in other examples, 92A-92C may have varying depths of penetration. In some examples, D2 may be at least about 0.030 inches. Other depths are contemplated. D1 and D2 in FIG. 3 may be substantially the same or different. Welds 92 may not penetrate through tabs 78 into plates 74.

Each anode electrode plate 74A includes a current collector (not shown) or grid, an electrode material and a tab 78A extending therefrom. Tab 78A comprises conductive material (e.g., titanium, etc.). Tab 78A comprises conductive material (e.g., copper, titanium, etc.). The electrode material (or anode material) may include elements from Group IA, IIA or IIIB of the periodic table of elements (e.g. lithium, sodium, potassium, etc.), alloys thereof, intermetallic compounds (e.g. Li—Si, Li—B, Li—Si—B etc.), or an alkali metal (e.g. lithium, etc.) in metallic form.

Each of welds 90B and 92B may penetrate through the tabs to pins 80 and 84, respectively, at each level of the stack. Put another way, weld 90B penetrates into each conductive tab 76 in the vertical stack of conductive tabs to pin 80, and weld 92B penetrates into each conductive tab 78 in the vertical stack of conductive tabs to pin 84. In the case of stacks including a spacer on the top and/or bottom tab of the stack, the weld may not melt the top surface of the top spacer or the bottom surface of the bottom spacer.

Figure 5:
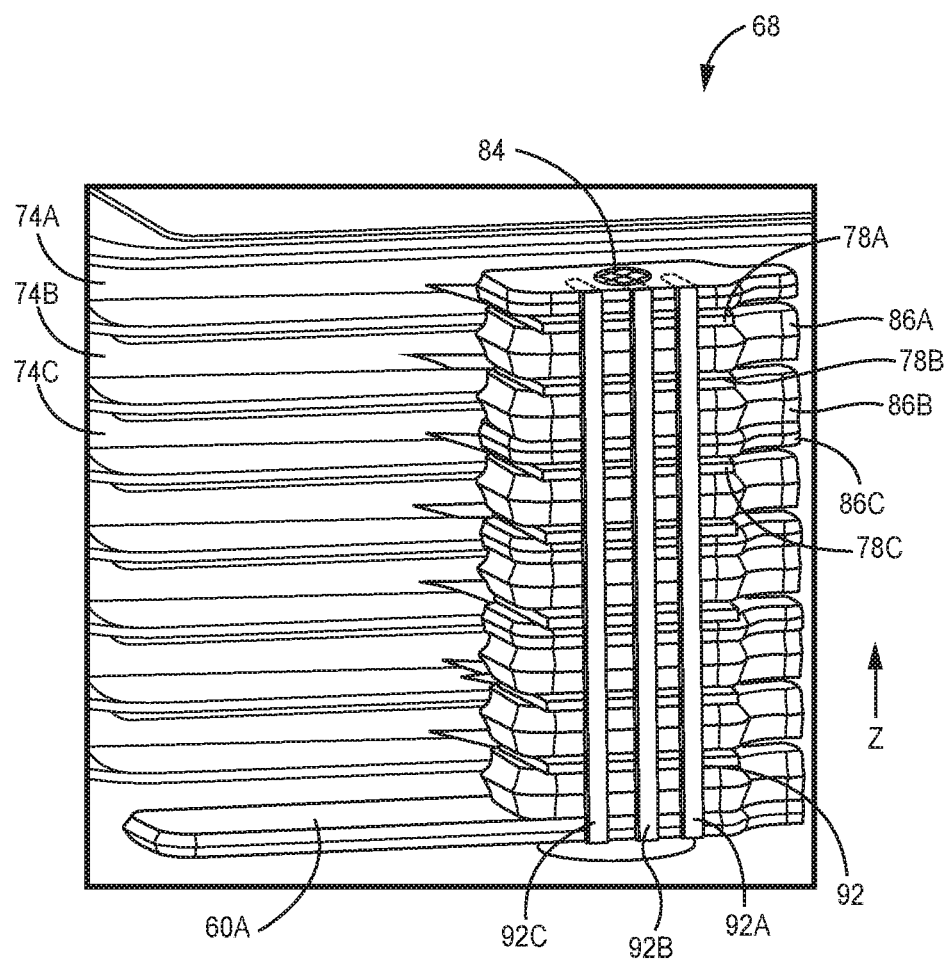
FIG. 5 is a conceptual diagram illustrating a portion of an example battery assembly including a stack of tabs and spacers of an electrode.
Figure 6:
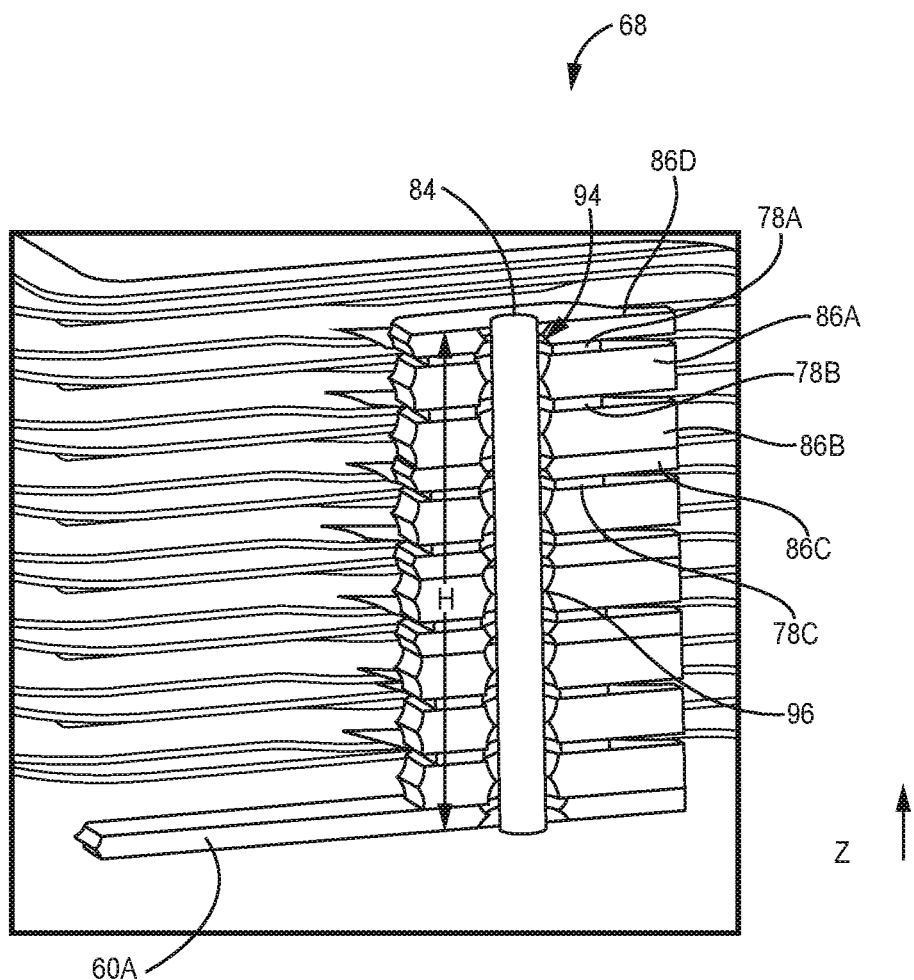
FIG. 6 is a conceptual diagram illustrating a cross-sectional view of the stack of tabs and spacers of FIG. 5.

FIG. 5 is a conceptual schematic diagram illustrating a magnified view of a portion of anode 68 of battery 26. FIG. 6 is a cross-section view of the stack of anode tabs 78 shown in FIG. 5. As shown, electrodes plates 74 of anode 68 includes anode electrode plates 74A, 74B, 74C (among others) in a stacked configuration. Anode tabs 78A, 78B, 78C extend from anode electrodes plates 74A, 74B, 74C, respectively, and exhibit the same stacked configuration as electrode plate 74. At least one spacer is located between each respective tab. For example, spacer 86A is located between tabs 78A and tab 78B, and two spacers 86B and 86C are located between tab 78B and tab 78C.

In some examples, the top end of alignment member 84 may be slightly higher than the top surface of the stack (e.g., the top surface of spacer 86D in FIGS. 5 and 6) but the bottom end of alignment member 84 may not extend beyond the bottom of the stack, e.g., the bottom spacer directly adjacent the top of conductive plate 60A, or may not extend beyond the bottom of conductive plate 60A. In some examples, the bottom spacer may be welded on a flat cover having a planar surface so that the extension of alignment member 84 beyond the bottom surface of the bottom spacer may cause issues for this welding to the flat cover.

For ease of description and illustration, not all the tabs and spacers of anode 68 are labelled in FIGS. 5 and 6. However, it is understood that the description of tabs 78A-78C and spacers 86A-86C also may apply to any of the tabs and spacers shown in FIGS. 5 and 6. Additionally, while FIG. 5 is described with regard to anode 68 it is contemplated that the same configuration is applicable to cathode 66 of battery 26 shown in FIG. 3.

In some examples, spacer 86A ensures tabs 78A and 78B are substantially straight extending from plates 74A and 74B, respectively, and are not bent during a subassembly process to connect the set of tabs 78 for anode 68. While a single spacer 86A is depicted as being placed between two tabs, more than one spacer may be placed between two tabs, such as, e.g., spacers 86B and 86C between tabs 78B and 78C.

Spacers 86A-86C may comprise a conductive material, e.g., such that the each of the tabs 78 are electrically interconnected at least in part via spacer 86. For electrode plates related to anode 68, titanium and alloys thereof or other suitable materials are used. For electrode plates related to anode 68, titanium, nickel, alloys thereof or other suitable materials are used.

Spacers 86A-86C may include a variety of shapes. Exemplary spacers include a substantially H-shaped spacer, substantially rectangular, circular, or include at least one triangular shape (e.g. a single triangle, a hexagon etc.). Spacers 86A-86C may have different or substantially the same individual thicknesses in the z-direction labeled in FIG. 5, e.g., to achieve different design criteria. For example, a thicker electrode plate may requires a thicker spacer. In the example in of FIG. 5, spacer 86A may have substantially the same thickness of spacer 86B but spacer 86C may be thinner than spacers 86A and 86B. Examples of spacers 86A-86C may include one or more of the example spacers described in U.S. Published Patent Application 2009/0197180.

As shown in FIGS. 5 and 6, anode 68 may include alignment member 84 extending through aperture 94 (shown in FIG. 4) that runs through anode tabs 78, spacers 86, and conductive plate 60A in the z-direction. Alignment member 84 and aperture 94 may be shaped such that alignment member 84 extends from the top to the bottom of the stack of tabs 78 and spacers 86 of anode 68. Alignment member 84 may be a solid body (e.g., as shown in FIG. 6) or a body that include an inner lumen. In some examples, alignment member 84 may be a solid pin with a substantially cylindrical shape and aperture 94 may have a circular cross-section. However, other shapes are contemplated for alignment member 84 and aperture 94, e.g., those having a square, rectangular, or triangular cross-section. In some examples, alignment member 96 may take the form of a rivet having a flanged head and tail portions on the top and bottom of the stack, respectively, that mechanically attaches the stack of tabs 78 and spacers 86 to each other.

As noted above, welds 92 penetrate into tabs 78. As shown in FIG. 5, welds 92 also penetrate into spacers 86 (including spacers 86A-86C). In such examples, spacers 86 may formed of material suitable for being welded to each other, tabs 78 and/or alignment member 84. Example materials for spacers 86 may include titanium.

Figure 7:
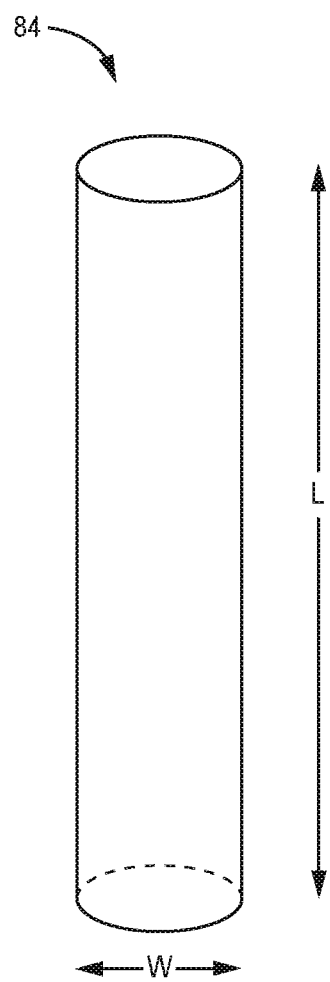
FIG. 7 is a conceptual diagram illustrating an example alignment member in accordance with an example of the disclosure.

FIG. 7 is a schematic diagram illustrating example alignment member 84 of anode 68. As shown, alignment member 84 has a length L and a width W. In the example of FIG. 7, alignment member is substantially cylindrical in shape where the width W is equal to the diameter of the cylindrical body. The length L of alignment member 84 may be approximately equal to the overall height H (labelled in FIG. 6) of the stack of tabs 78, spacers 86, and conductive member 60A. In other examples, the length L of alignment member 84 may be greater than the overall height H, e.g., to allow the top of alignment pin to slightly protrude from the top of the stack, e.g., from the top of spacer 86D. The width W may be less than the corresponding width of aperture 94 defined through the stack of tabs 78, spacers 86, and conductive member 60A such that alignment member 84 fits within aperture 94. As shown, the width W of alignment member 84 is substantially uniform along the length L. In some examples, the gap between the outer perimeter of alignment member 84 and the corresponding aperture 94 may be substantially constant throughout the height of stack. Too large of gap may cause difficulties in welding. The alignment member 84 and corresponding aperture 84 do not need to be round in shape and may be other matching shapes, such as, rectangular or oval.

In some examples, the length L of alignment member 84 may be about the same or the same as the height H of the stack or slightly taller, e.g., about 0.010 inches taller. In some examples, the width W of alignment member 84 may be about 0.020 inches to about 0.050 inches. Other values are contemplated. The size and shape of alignment member 80 may be substantially the same or different than that of alignment member 84.

Figure 8:
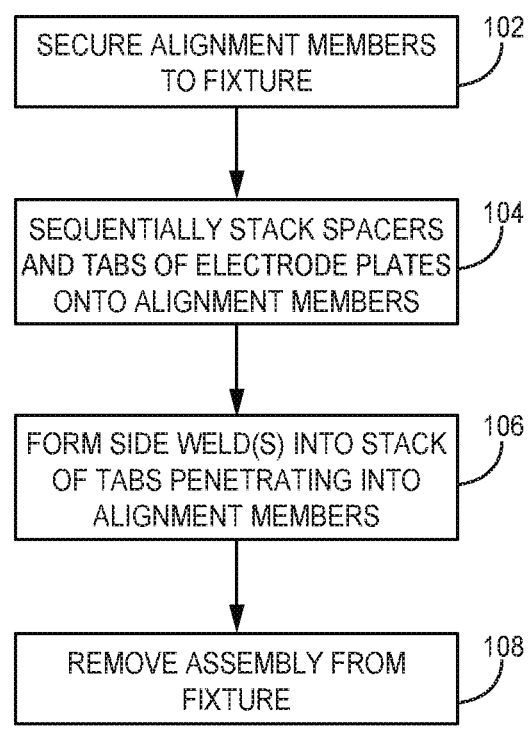
FIG. 8 is a flowchart illustrating an example technique in accordance with examples of the disclosure.

FIG. 8 is an example flow diagram illustrating an example technique for assembling battery 26 using alignment members 84 and 80. As shown, alignment members 84 and 80 may be removably secured to a fixture holding each alignment member vertically with spacing between the respective alignment members according to the gap between alignment member 84 and 80 shown, e.g., in FIG. 3 (102). The individual plates of electrodes plates 74 and 72 and corresponding spacers (e.g., spacers 86) may be sequentially stack onto each other by placing a tab 76 of one of plates 72 onto alignment member 80 followed by placement of a tab 78 of one or plates 74 onto alignment member 84, as so forth, along with one or more spacers between the tabs to arrive at the assembly shown in FIGS. 3-6 (104). In each case, the individual aperture formed in respective tab 78 or 76 may be placed onto the corresponding alignment member 84 or 80 so that the alignment member 84 or 80 extends through the aperture of tab 78 or 76. Individual spacers 86 may be placed onto alignment members 84 and 80, as desired, between respective tabs. In other examples, a stack alternating between plates 72 and plates 74 may be roughly stacked onto each other than then placed onto alignment members 84 and 80 such that the alignment members 84 extend through the apertures in the stack of tabs 78 and 76 rather than sequentially assembling plates 72 and 74.

Once plates 72 and 74 have been assembled onto alignment members 80 and 84, respectively, side welds 90 and 92 may be formed into the stack of tabs 76 and 78 (106). Any suitable technique may be employed to form welds 90 and 92 including, e.g., laser welding or electron beam welding. In the case of battery assembly, the welding process may be controlled such that weld 92B penetrates into alignment member 84 and weld 90B penetrates into alignment member 80. Conversely, welds 92A and 92C may be formed adjacent to alignment member 84 and welds 90A and 90C may be formed adjacent to alignment member 80, as shown, e.g., in FIG. 3. Once welds 90 and 92 have been formed, the assembly may be removed from the fixture within alignment members 80 and 84 welded to the stacks of tabs 76 and 78, respectively (108). The two stacks may then be welded to conductive members 60A and 60B as shown in FIGS. 3 and 4, for example. Bottom housing portion 50A and top housing portion 50B may then be subsequently welded to enclose the assembly within and form battery 26.

In another example, alignment members 80 and 84 may be in continuous form that is fed into proper height from the bottom of the fixture. After welding, the pin is cut off flush at the bottom of the stack.

Various examples have been described in the disclosure. These and other examples are within the scope of the following claims.

The invention claimed is:

1. A battery assembly for an implantable medical device, the assembly comprising:
    an electrode stack comprising a plurality of electrode plates, wherein the plurality of electrode plates comprises a first electrode plate including a first tab extending from the first electrode plate and a second electrode plate including a second tab extending from the second electrode plate;
    an alignment pin extending through a first aperture in the first tab and a second aperture in the second tab; and
    a weld on a side of the electrode stack extending from the first tab to the second tab, wherein the weld penetrates into the alignment pin.

2. The assembly of claim 1, further comprising a spacer between the first tab and the second tab, wherein the weld extends from the first tab to the second tab across the spacer.

3. The assembly of claim 1, wherein the alignment pin comprises an electrically conductive material that electrically couples the first tab and the second tab.

4. The assembly of claim 1, wherein the weld comprises a first weld, the assembly further comprising at least one second weld on the side of the electrode stack extending from the first tab to the second tab.

5. The assembly of claim 1, wherein the alignment pin has a substantially cylindrical shape with a substantially uniform diameter.

6. The assembly of claim 1, wherein the alignment pin comprises titanium.

7. The assembly of claim 1, wherein the first electrode plate comprises a first anode electrode plate and the second electrode plate comprises a second anode electrode plate.

8. The assembly of claim 7, wherein the alignment pin comprises a first alignment pin and the weld comprises a first weld, wherein the plurality of electrode plates further comprises a first cathode plate including a third tab extending from the first cathode plate and a second cathode plate including a fourth tab extending from the second cathode plate, wherein the third tab and second tab are stacked adjacent to the first tab and second tab, the assembly further comprising:
    a second alignment pin extending through a third aperture in the third tab and a fourth aperture in the fourth tab, and
    a second weld on the side of the electrode stack extending from the third tab to the fourth tab, wherein the second weld penetrates into the second alignment pin.

9. The assembly of claim 1, wherein the weld comprises a laser weld.

10. A method for forming a battery assembly, the method comprising:
    assembling an electrode stack on an alignment pin, the electrode stack comprising a plurality of electrode plates, wherein the plurality of electrode plates comprises a first electrode plate including a first tab extending from the first electrode plate and a second electrode plate including a second tab extending from the second electrode plate, wherein the alignment pin extends through a first aperture in the first tab and a second aperture in the second tab when the electrode stack is assembled; and
    welding a side of the electrode stack to form a weld that penetrates into the alignment pin through the first tab and the second tab.

11. The method of claim 10, wherein assembling the electrode stack on the alignment pin comprises stacking the first tab and the second tab on the alignment pin.

12. The method of claim 10, wherein welding the side of the electrode stack comprises laser welding the side of the electrode stack.

13. The method of claim 10, wherein stacking the first tab and the second tab on the alignment member comprises iteratively stacking the first tab and the second tab on the alignment pin.

14. The method of claim 10, wherein assembling the electrode stack comprises placing a spacer between the first tab and the second tab, wherein the weld extends from the first tab to the second tab across the spacer.

15. The method of claim 10, wherein the alignment pin comprises an electrically conductive material that electrically couples the first tab and the second tab.

16. The method of claim 10, wherein the weld comprises a first weld, the method further comprising welding the side of the electrode stack to form at least one second weld on the side of the electrode stack extending from the first tab to the second tab but not into the alignment pin.

17. The method of claim 10, wherein the alignment pin has a substantially cylindrical shape with a substantially uniform diameter.

18. The method of claim 10, wherein the alignment pin comprises titanium.

19. The method of claim 10, wherein the first electrode plate comprises a first anode electrode plate and the second electrode plate comprises a second anode electrode plate.

20. An implantable medical device comprising:

an outer housing;

processing circuitry; and the battery assembly of claim 1 within the outer housing, wherein the processing circuitry is configured to control delivery electrical therapy from the implantable medical device to a patient using power supplied by the battery assembly.

* * * * *